(12) United States Patent
Spiridigliozzi et al.

(10) Patent No.: US 8,182,524 B2
(45) Date of Patent: May 22, 2012

(54) STENT-GRAFT WITH ADJUSTABLE LENGTH

(75) Inventors: John Spiridigliozzi, Sharon, MA (US);
William R. Quinn, Swampscott, MA (US); Orla McCullagh, Waltham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 73 days.

(21) Appl. No.: 12/842,819

(22) Filed: Jul. 23, 2010

(65) Prior Publication Data

US 2011/0015719 A1      Jan. 20, 2011

Related U.S. Application Data

(63) Continuation of application No. 10/116,373, filed on Apr. 4, 2002, now Pat. No. 7,789,903.

(51) Int. Cl.
*A61F 2/06* (2006.01)
(52) U.S. Cl. ...................... 623/1.13; 623/1.35
(58) Field of Classification Search ................ 623/1.15, 623/1.13, 1.18, 1.2, 1.3, 1.31, 1.35, 1.44
See application file for complete search history.

(56) References Cited

U.S. PATENT DOCUMENTS

| | | | |
|---|---|---|---|
| 5,360,443 A | 11/1994 | Barone et al. | |
| 5,499,995 A | 3/1996 | Teirstein | |
| 5,653,743 A | 8/1997 | Martin | |
| 5,683,448 A | 11/1997 | Cragg | |
| 5,693,087 A | 12/1997 | Parodi | |
| 5,755,773 A | 5/1998 | Evans et al. | |
| 5,817,126 A | 10/1998 | Imran | |
| 5,906,641 A | 5/1999 | Thompson et al. | |
| 5,993,481 A | 11/1999 | Marcade et al. | |
| 6,036,723 A | 3/2000 | Anidjar et al. | |
| 6,102,938 A | 8/2000 | Evans et al. | |
| 6,110,198 A | 8/2000 | Fogarty et al. | |
| 6,132,459 A | 10/2000 | Piplani et al. | |
| 6,159,238 A | 12/2000 | Killion et al. | |
| 6,200,339 B1 | 3/2001 | Leschinsky et al. | |
| 6,302,917 B1 | 10/2001 | Dua et al. | |

FOREIGN PATENT DOCUMENTS

EP      1029518      8/2000

OTHER PUBLICATIONS

U.S. Appl. No. 09/442,165, filed Nov. 16, 2002, by Paul F. Chouinard, et al. U.S. Appl. No. 09/702,226, filed Oct. 31, 2000, by Steven E. Walak.
Parodi, Juan Carlos, "Endovascular Repair of Abdominal Aortic Aneurysms and Other Arterial Lesions," J.Vasc. Surg. 21:549-57 (Apr. 1995). Printed from Journal of Vascular Surgery Online.
International Search Report for corresponding International Application PCT/US03/08579, mail date Sep. 5, 2003.

*Primary Examiner* — Julian Woo
(74) *Attorney, Agent, or Firm* — Brooks, Cameron & Huebsch, PLLC

(57) ABSTRACT

A stent-graft comprising a stent and a graft having a supported portion lining or covering at least a portion of the stent, and an unsupported portion extending proximally beyond the proximal end of the stent. The stent-graft may have a length corresponding to at least a mean standard length from a standard incision point to a distal-most portion of a standard lumen into which the distal end of the stent is adapted to be deployed, with the unsupported portion of the graft extending beyond the mean standard length by an amount equal to at least two, if not three or more, standard deviations of the mean standard length. A method for deploying the stent-graft comprises making an incision in a wall of the lumen, introducing and deploying the stent-graft in the lumen so that the proximal end extends beyond the incision, and attaching the graft to a lumen by anastamosis.

25 Claims, 2 Drawing Sheets

STENT-GRAFT WITH ADJUSTABLE LENGTH

CROSS-REFERENCE TO RELATED APPLICATIONS

This application is a continuation of U.S. patent application Ser. No. 10/116,373, filed Apr. 2, 2002, which is herein incorporated by reference.

TECHNICAL FIELD

This invention relates generally to endoluminal devices and, more specifically, to stent-grafts having an adjustable length.

BACKGROUND OF THE INVENTION

A stent is an elongated device used to support an intraluminal wall. In the case of a stenosis, a stent provides an unobstructed conduit through a body lumen in the area of the stenosis. Such a stent may also have a prosthetic graft layer of fabric or covering lining the inside and/or outside thereof. Such a covered stent is commonly referred to in the art as an intraluminal prosthesis, an endoluminal or endovascular graft (EVG), or a stent-graft.

A stent-graft may be used, for example, to treat a vascular aneurysm by removing the pressure on a weakened part of an artery so as to reduce the risk of rupture. Typically, a stent is implanted in a blood vessel at the site of a stenosis or aneurysm endoluminally, i.e. by so-called "minimally invasive techniques" in which the stent, restrained in a radially compressed configuration by a sheath or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means. The term "proximal" as used herein refers to portions of the stent or delivery system relatively closer to the end outside of the body, whereas the term "distal" is used to refer to portions relatively closer to the end inside the body.

When the introducer has been threaded into the body lumen to the stent deployment location, the introducer is manipulated to cause the stent to be ejected from the surrounding sheath or catheter in which it is restrained (or alternatively the surrounding sheath or catheter is retracted from the stent), whereupon the stent expands to a predetermined diameter at the deployment location, and the introducer is withdrawn. Stent expansion may be effected by spring elasticity, balloon expansion, or by the self-expansion of a thermally or stress-induced return of a memory material to a pre-conditioned expanded configuration.

Among the many applications for stent-grafts is that of deployment in lumen for repair of aneurysms, such as abdominal aortic aneurysms (AAA). One approach for isolating AAA aneurysms was described by Dr. Juan Parodi in "Endovascular Repair of Abdominal Aortic Aneurysms and Other Arterial Lesions", J. Vasc. Surg. 21: 549-57 (April, 1995), incorporated herein by reference. This method, also known as an "aorto-uni-iliac" method, involves deploying an unbranching tubular prosthesis from the healthy aorta above the aneurysm, through the aneurysm, and into one of the two iliac arteries, so that all the blood flowing through the aorta goes into that single iliac. A portion of the blood is then transferred to the opposite portion of the vascular system (normally supplied by the opposite iliac) through a "femorofemoral bypass," such as a prosthetic vascular graft having an end-to-side anastomosis with each of the femoral arteries. Advantageously, known femorofemoral bypass procedures involve substantially less patient trauma than conventional invasive aortic aneurysm repair. The unused iliac artery is then occluded with detachable balloons, ligation, or any other occlusion devices known in the art, such as but not limited to devices described in U.S. Pat. No. 5,499,995, incorporated herein by reference. Other methods and systems are known in the art for converting a bifurcated prosthesis to a single-lumen prosthesis for use with the above techniques when deployment of a bifurcated prosthesis is aborted after deployment of a first portion of the prosthesis, as described in U.S. Pat. No. 5,755,773 to Evans et al., also incorporated herein by reference.

Current endovascular treatment of aneurysms is sometimes contra-indicated, however, due to severe occlusive disease or tortuosity, such as in the iliac artery. Detailed measurements are typically required prior to performing the treatment. Additionally, a large inventory of size configurations may be required on hand to be able to address the variety of patients that may be encountered. The above drawbacks may preclude use of emergent techniques if the facility does not have the entire matrix of sizes available on hand at the time the procedure needs to be performed. Problems associated with a lack of having a particular size available may be exacerbated in the event of an aneurysm rupture that must be repaired immediately.

It is therefore desirable to provide a single stent-graft design that is adjustable so that one size can fit a larger percentage of patients than existing designs.

SUMMARY OF THE INVENTION

In accordance with this invention, there is provided a stent-graft adapted for implantation in a distal location in a lumen from a proximal introduction site. The stent-graft comprises a stent having a distal end and a proximal end; and a graft having a supported portion lining or covering at least a portion of the stent, and an unsupported portion extending proximally beyond the proximal end of the stent.

In various embodiments, the stent-graft may have one or more or all of the following features. The stent may comprise a braided architecture and the distal end may comprise a wound end section, such as having a hexagonal cell architecture. The stent distal end may extend distally beyond a distal end of the graft. The unsupported portion of the graft may have a length sufficient to extend at least from the proximal end of the stent to the incision through which the stent-graft is adapted to be implanted in the lumen. The stent-graft may have a length corresponding to at least a mean standard length from a standard location for the incision point to a distalmost portion of a standard lumen into which the distal end of the stent is adapted to be deployed, and the unsupported portion may extend beyond the mean standard length by an amount equal to at least two, if not three or more, standard deviations of the mean standard length. The lumen may comprise an aorta and the stent-graft may be adapted for aorto-uni-iliac treatment of an abdominal aortic aneurysm, the stent-graft having a length extending from a distal anchoring point distal of the aneurysm to a proximal anchoring point in an iliac artery distal of a femoral branch.

A method for deploying the stent-graft of this invention comprises making an incision in a wall of the lumen; introducing the stent-graft into the lumen; deploying the stent-graft in the lumen such that an extension of the unsupported portion of the graft extends through the incision in the lumen wall; and severing the lumen and attaching a proximal end of the graft to a distal end of a lumen by anastamosis. In an embodiment wherein the lumen comprises an aorta and the method comprises aorto-uni-iliac treatment of an abdominal aortic aneurysm, the method comprises deploying the distal end of the stent distal of the aneurysm and deploying the proximal end of the stent in a first iliac artery. Such a method further comprises the steps of deploying an occluder in a second iliac artery to prevent reverse vascular flow into the aneurysm; and providing one or more bypasses to provide vascular flow from the first iliac to the second iliac and to any other lumen occluded by installation of the stent-graft.

It is to be understood that both the foregoing general description and the following detailed description are exemplary, but not restrictive, of the invention.

BRIEF DESCRIPTION OF THE DRAWINGS

The invention is best understood from the following detailed description when read in connection with the accompanying drawing, in which.

DETAILED DESCRIPTION OF THE INVENTION

The invention will next be illustrated with reference to the figures wherein the same numbers indicate similar elements in all figures. Such figures are intended to be illustrative rather than limiting and are included herewith to facilitate the explanation of the apparatus of the present invention.

Figure 1:
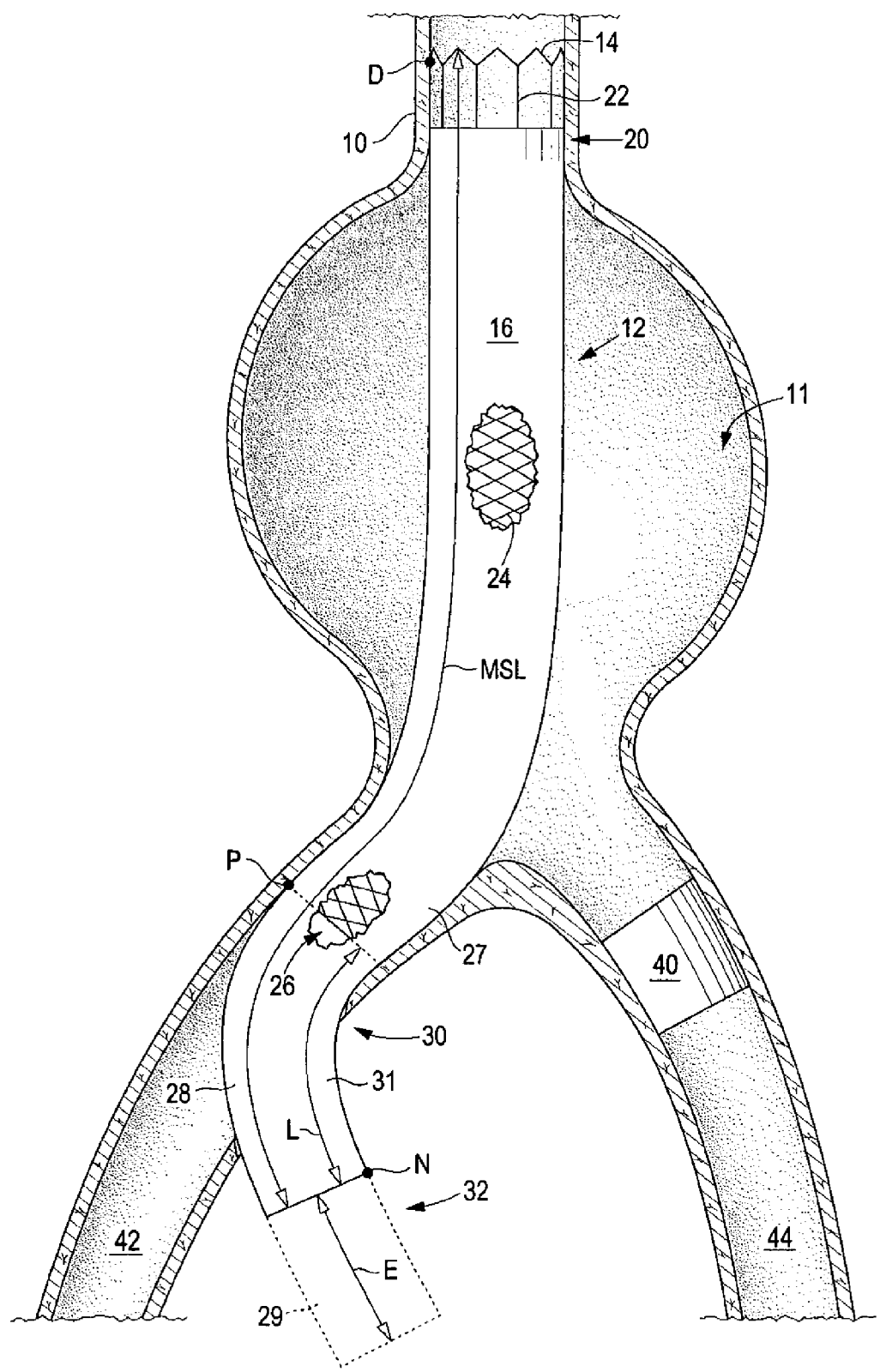
FIG. 1 is an illustration of a longitudinal section of an aorta having an aneurysm, showing an exemplary device of the present invention deployed therein.

Referring now to FIG. 1 there is shown a cross-section of an exemplary lumen 10 (in this case, an aorta) with an aneurysm 11 and having deployed therein a stent-graft 12 of the present invention. Stent-graft 12 is adapted for aorto-uni-iliac treatment of an abdominal aortic aneurysm (AAA) and comprises a stent 14 and a graft 16. Graft 16, shown as an outer covering on stent 14 in FIG. 1, may comprise an inner lining or an outer covering, and stent 14 may have some combination of inner graft lining and outer graft covering. The portion of graft 16 covering or lining stent 14 is referred to herein as the "supported" portion 27. Graft 16 extends proximally beyond the proximal end 26 of stent 14 to form an "unsupported" portion 28. Unsupported portion 28 may extend as long as desired, to allow it to be tailored by the clinician implanting stent-graft 12.

Stent 14 may protrude from graft 16 at distal end 20 of stent-graft 12, such as to allow intraluminal tissue growth (not shown) to provide additional anchoring for the stent as is known in the art. As shown in FIG. 1, stent 14 comprises a hybrid stent having a wound distal end section 22, a braided midsection 24, and a braided proximal end. Hybrid braided/wound stents are described in U.S. patent application Ser. No. 09/442,165, filed Nov. 16, 1999, by Chouinard et al., assigned to the assignee of this invention and incorporated by reference. The particular architecture shown in FIG. 1 comprises a wound end section 22 comprising a hexagonal cell architecture. The term "midsection" may be used herein to refer to any portion of the stent-graft between the proximal and the distal ends.

The invention is not limited to any particular stent architecture, however, and may include filamentary or cut tube architectures, including non-hybrid filamentary stents that are wound or braided along their entire length. Although hybrid stents in which the wound end section and braided midsection are connected by one or more continuous filaments running through both sections as disclosed in the '165 Application are advantageous, the invention is not limited to such a configuration. Rather, distal end section 22 may be a separate and distinct stent from midsection 24, with those sections attached together by common attachment to the graft 16, as described in the '165 application, or by some other means of attaching section 22 directly to midsection 24, such as but not limited to with sutures, staples, wire, adhesive, welding, or any other method known in the art.

In a typical method of deploying one stent-graft embodiment of this invention, a clinician makes an incision 30 in lumen 10, such as in left iliac artery 42 as shown in FIG. 1, through which stent-graft 12 is introduced. The stent-graft may be introduced by any method known in the art, using any introducer known in the art, such as but not limited to introducers guided by guidewires. Typically, distal end 22 of stent 14 is deployed first, and stent-graft 12 is deployed from distal end 22 to proximal end 26, with an extension 31 of the unsupported portion 28 of graft 16 extending through incision 30 and beyond. The introducer and any guidewires associated therewith may be removed from the lumen after the stent-graft has been fully deployed. The clinician may then cut any amount of excess portion 29 of unsupported portion 28 that is not needed, and sever the body lumen at a location desired for joining by anastomosis with the proximal end 32 (which may be the original end or the cut end) of graft 16. In this way, the overall length of stent-graft 12 is adjusted to fit the particular application.

For a AAA application, as shown in FIG. 1, stent-graft 12 is deployed to span at least a length from anchoring point D distal of the aneurysm to anchoring point P in left iliac. Because of the difference in diameter at the trunk of the aorta near anchoring point D as compared to the diameter of the iliac at anchoring point P, stent 14 may be tapered from its distal end 22 to its proximal end 26. Anchoring point P is typically distal of the point where the femoral artery (not shown) branches off of the iliac. It should be understood, however, that the anchoring point P may be in the right iliac and/or may be proximal of the femoral artery, and that the invention is not limited to any particular orientation or location of deployment. Because deployment of a single lumen stent-graft necessarily connects the aortic trunk to only a single iliac, occluder 40 is typically deployed in the opposite iliac to stop vascular flow to the aneurysm. A bypass from left iliac 42 to right iliac 44 is also typically performed to provide blood flow to the opposite iliac, such as a bypass from the right femoral artery (not shown) to the left femoral artery (not shown). Procedures for deployment of the occluder and bypasses from one iliac to the other are well known in the art, as discussed in the Background section of this disclosure and in the references disclosed therein and incorporated by reference.

The length of unsupported portion 28 may be any length sufficient to extend at least a length L from proximal end 26 of stent 14 through typical incision 30, preferably with some amount of excess 29 having a length E built in as a safety factor. Excess length E is preferably at least as long as two standard deviations of the mean standard length MSL from a standard end point N that is 2 to 3 centimeters proximal of a standard location for incision 30, to a standard distalmost anchoring point D on a standard lumen into which distal end 22 of the stent is to be deployed. A length of two standard deviations for excess length E ensures that the overall length of stent-graft 12 will be adequate for at least 95% of all applications. More preferably, excess length E is at least as long as three standard deviations, so the overall length is adequate for at least 99% of all applications. Excess length E is not limited to any particular length, however, and may be longer than three standard deviations for even added applicability.

The "mean standard length" as referred to herein, corresponds to the statistical arithmetic mean for a distribution of standard lengths from point N to point D as defined above for a statistically significant number of patients. A "statistically significant" number of patients may comprise any number of patients above a minimum number determinable by those skilled in the field of statistics as being a minimum number required for the number to be considered a legitimate sampling of individuals. "Standard deviation" as referred to herein is, by definition, the statistical measure of variability equal to the square root of the arithmetic average of the squares of the deviations from the mean standard length in the frequency distribution of standard lengths for the statistically significant number of patients, as is known in the art. The field of statistics is well known and is therefore not detailed any further herein.

The length of stent 14 is at least as long as a mean standard length required to span the distance between points D and P for standard such applications, optionally with some additional length to account for at least two, if not three or more standard deviations from the mean standard length, similar to the dimensions for the graft. Stent-grafts having a combination of a stent length designed to fit 99% of the standard spans required to anchor the stent at opposite ends of the aneurysm, combined with grafts having a length sufficient to extend at least to the incision point in 99% of standard applications, provides a single stent-graft that fits almost all patients for aorto-uni-iliac AAA treatment.

The remaining procedure is dependent upon the specific application, and the extent of disease in the patient. For example, if the disease in left iliac 42 shown in FIG. 1 does not extend proximally of the femoral branch (not shown) of the left iliac, then the left iliac 42 may be severed distally of the femoral branch, and the graft cut accordingly, if necessary, so that the end of the graft can be attached by anastamosis directly to the distal end of the severed iliac artery distal of the femoral branch. A bypass from the left femoral to the right femoral branch may then be performed to provide the full range of blood flow needed by the patient. If the disease in the left iliac 42 extends proximally of the femoral branch, then the left iliac is typically severed proximally of the femoral branch and the end of the graft attached to the distal end of the severed left iliac proximal of the femoral branch by anastamosis. Bypasses are then typically provided to both the left femoral artery and the right iliac (such as to the right femoral artery) to restore blood flow to the occluded lumens.

The graft may be a braided or non-braided graft, and may comprise any graft material known in the art. Suitable graft materials include, but are not limited to, polyethyleneterepthalate (PET), polyetheretherketone (PEEK), polysulfone, polytetrafluroethylene (PTFE), expanded polytetrafluroethylene (ePTFE), fluorinated ethylene propylene (FEP), polycarbonate urethane, a polyolefin (such as polypropylene, polyethylene, or high density polyethylene (HDPE)), silicone, and polyurethane. Yarns for braided grafts may comprise monofilaments or multifilament yarns, either with round or non-round cross-section, and multifilament yarns may comprise twisted or untwisted filaments.

The stent may comprise any material known in the art, including but not limited to self-expanding metals such as nitinol, balloon-expandable materials such as stainless steel, or even non-metals, such as polymer materials. The stent may also comprise a hybrid self-expanding, balloon-expandable design, having at least one superelastic section and at least one plastically deformable section, such as but not limited to those described in U.S. patent application Ser. No. 09/702,226, by Steven E. Walak, filed Oct. 31, 2000, assigned to the common assignee of this invention, and incorporated herein by reference.

Although generally described herein with respect to a single-lumen stent-graft having its distal end deployed above the aneurysm and its proximal end deployed in the iliac, the present invention is also applicable to convert a bifurcated prosthesis to a single lumen prosthesis, such as in applications wherein it is determined after deployment of a trunk portion of a bifurcated prosthesis that completion of the bifurcated device is not desired. U.S. Pat. No. 5,755,773 describes some scenarios under which this may occur. In such cases, the distal end of a stent-graft embodiment of this invention may be adapted for deployment within a bifurcated prosthesis, consistent with any of the embodiments shown and described in the '773 patent which substantially seal one of the two branches of the bifurcated prosthesis to prevent fluid passage into the second branch. The proximal end of such a stent-graft, however, comprises an unsupported graft portion of the present invention that extends beyond the proximal end of the stent and can be tailored to any length required, as disclosed herein.

Figure 2:
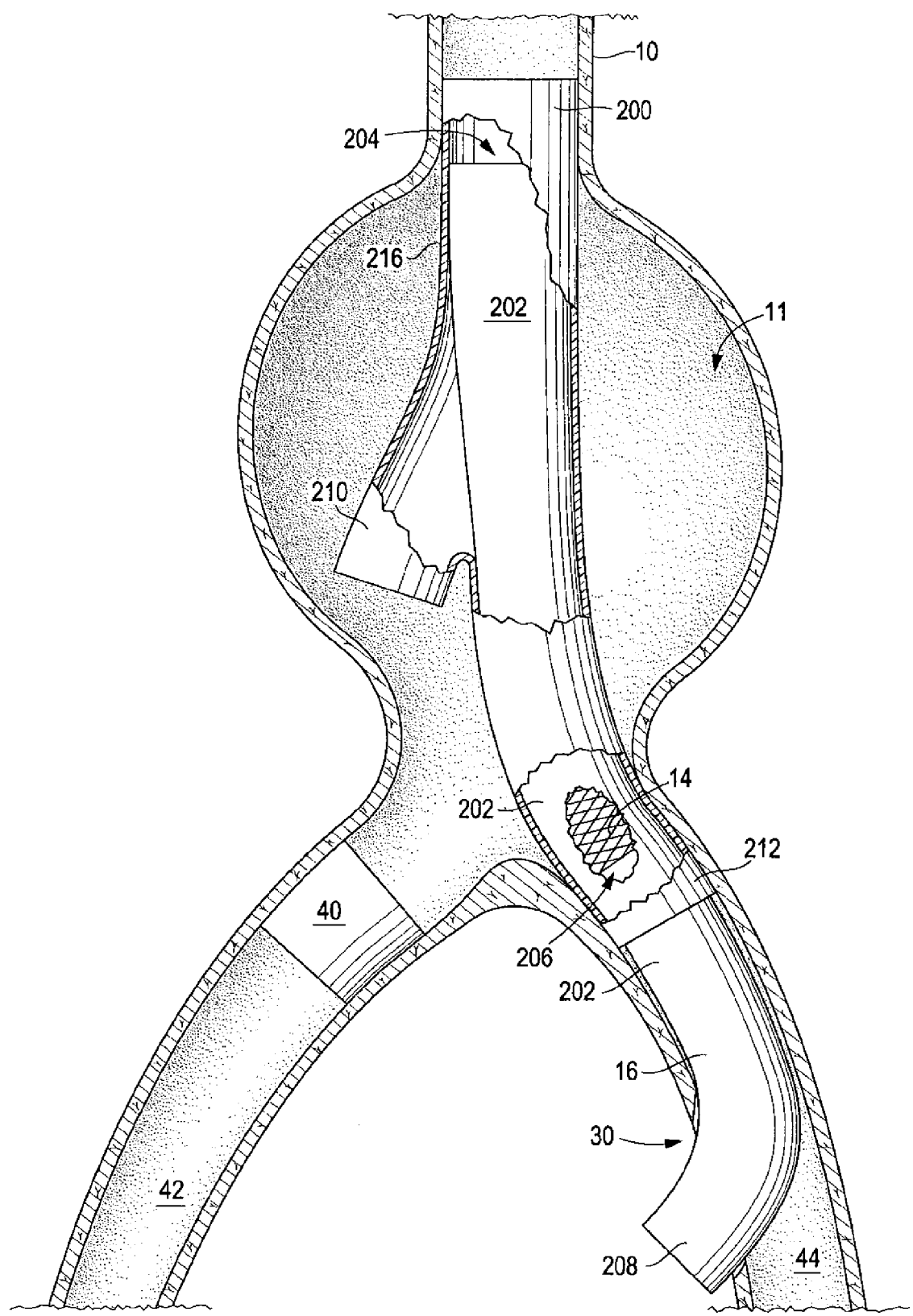
FIG. 2 is an illustration of a longitudinal section of an aorta having an aneurysm, showing an exemplary device of the present invention deployed inside a portion of a bifurcated prosthesis.

FIG. 2 shows an exemplary such embodiment, comprising bifurcated prosthesis 200 in partial cross-section, stent-graft 202 for conversion of the bifurcated prosthesis to a single-lumen device, distal end 204 of the stent-graft for implantation within the bifurcated prosthesis, proximal end 206 of stent 14, and unsupported region 208 of graft 16 extending outside of the incision 30. Such a device may provide an advantageous method for avoiding more invasive surgery when it is discovered after implantation of a portion of a bifurcated device, that the procedure cannot be completed. Although bifurcated prosthesis 200 is shown as having one short stump 210 and one long leg 212 implanted in iliac artery 44, the bifurcated prosthesis may have two short stumps, two long legs, or the long leg may be deployed in iliac artery 42 rather than 44.

Although shown with the distal end 204 of stent-graft 202 implanted in trunk section 216 of bifurcated prosthesis 200, a stent-graft 12 such as shown in FIG. 1 may simply be extended through the bifurcated prosthesis with its distal end 204 implanted directly in lumen 10 distal of the bifurcated prosthesis. In such case, the design of a stent-graft for deploying in a bifurcated prosthesis may be essentially the same as that for deployment directly in a lumen. The advantage of stent-graft 12 being designed with a length longer than needed to fit the majority of applications, means that an off-the-shelf component may span the distance from a location distal of the distal end of bifurcated prosthesis 200 to a point located proximal of incision 30 proximal of the proximal end of the bifurcated prosthesis. Thus, a single commercial embodiment of the stent-graft of the present invention may not only eliminate the need for a hospital to stock numerous sizes of aorto-uni-iliac stent-grafts, but also may eliminate the need to stock specific shunts for converting bifurcated stent-grafts to aorto-uni-iliac stent-grafts.

Furthermore, although illustrated and described herein with reference to certain specific embodiments, the present invention is nevertheless not intended to be limited to the details shown. Rather, various modifications may be made in the details within the scope and range of equivalents of the claims and without departing from the spirit of the invention.

For example, although illustrated and described herein predominantly with respect to vascular applications generally, and specifically with respect to aorto-iliac applications, it should be understood that the apparatus and methods of this invention are not limited to use in any particular body lumens, and thus may be applicable to vascular and non-vascular applications alike. Additionally, although advantageously shown and described herein with respect to single lumen devices, the present invention may also be applied to devices with multiple lumens such as bifurcated devices.

What is claimed is:

1. A stent-graft adapted for implantation in a distal location in an aorta from a proximal introduction site for aorto-uni-iliac treatment of an abdominal aortic aneurysm, the stent-graft comprising:
   a stent having a distal end, a proximal end, and a length sufficient to extend from a distal anchoring point in the aorta distal of the aneurysm to a proximal anchoring point in an iliac artery, the distal end of the stent having a first diameter sized to peripherally engage the aorta, and the proximal end of the stent having a second diameter smaller than the first diameter and sized to peripherally engage the iliac artery, wherein the stent comprises a braided architecture and the distal end comprises a wound end section; and
   a graft having a supported portion lining or covering at least a portion of the stent and an unsupported portion extending proximally beyond the proximal end of the stent, wherein the unsupported portion has a means for allowing cutting of its length within a patient's body and enables an overall length of the stent-graft to be adjusted.

2. The stent-graft of claim 1, wherein the wound end section comprises a hexagonal cell architecture.

3. The stent-graft of claim 2, wherein the wound end section and the braided section are connected by at least one common filament contained in both the wound end section and the braided section.

4. The stent-graft of claim 1, wherein the unsupported portion of the graft extends beyond a mean standard length by an amount equal to at least two standard deviations of the mean standard length.

5. The stent-graft of claim 1, wherein the unsupported portion of the graft extends beyond a mean standard length by an amount equal to three or more standard deviations of the mean standard length.

6. The stent-graft of claim 1, wherein the stent comprises a balloon-expandable material.

7. The stent-graft of claim 6, wherein the balloon-expandable material comprises stainless steel.

8. The stent-graft of claim 1, wherein the graft comprises a material comprising a polyolefin selected from the group consisting of: polypropylene, polyethylene, or high density polyethylene (HDPE).

9. The stent-graft of claim 1, wherein the stent is tapered from its distal end to its proximal end.

10. The stent-graft of claim 1, wherein the stent has a length sufficient to extend downstream beyond a femoral branch in the iliac artery.

11. The stent-graft of claim 10, wherein the stent extends beyond a mean standard length by an amount equal to at least two standard deviations of the mean standard length.

12. The stent-graft of claim 10, wherein the stent extends beyond a mean standard length by an amount equal to three or more standard deviations of the mean standard length.

13. The stent-graft of claim 1, wherein the stent-graft is adapted for aorto-uni-iliac treatment of an abdominal aortic aneurysm, the stent having a length for extending from a distal anchoring point distal of the aneurysm to a proximal anchoring point in an iliac artery.

14. The stent-graft of claim 1, wherein the stent-graft is adapted for conversion of a bifurcated prosthesis to a single lumen prosthesis, the bifurcated prosthesis having a trunk, a first depending portion, and a second depending portion, the stent-graft having a proximal end for deploying in the trunk of the bifurcated prosthesis, a midsection for extending through the first depending portion and for substantially sealing off the second depending portion from communication of fluid thereto from the trunk, and a proximal end for extending through an incision in the lumen into which the stent-graft is implanted.

15. The stent-graft of claim 1, wherein the stent-graft is sized for deployment in the aorta extending into a first iliac artery and an occluder device is sized for deployment in a second iliac artery.

16. A stent-graft for aorto-uni-iliac treatment of an abdominal aortic aneurysm, the stent-graft adapted for implantation in a distal location in a lumen from a proximal introduction site, the stent-graft comprising:
   a stent having a wound distal end, a braided midsection, and a proximal end, the stent having a length sufficient to extend from a distal anchoring point in the aorta distal of the aneurysm to a proximal anchoring point in an iliac artery distal of a femoral branch in the iliac artery, the distal end of the stent having a first diameter sized to peripherally engage the aorta and the proximal end of the stent having a second diameter smaller than the first diameter and sized to peripherally engage the iliac artery; and
   a graft having a supported portion lining or covering the stent from the stent proximal end to a location proximally adjacent an uncovered or unlined stent distal end, and an unsupported portion extending proximally beyond the proximal end of the stent and having a length sufficient to extend proximally beyond the femoral branch in the iliac artery, wherein the unsupported portion has a means for allowing cutting of its length within a patient's body and enables an overall length of the stent-graft to be adjusted.

17. The stent-graft of claim 16, wherein the stent comprises nitinol and the graft comprises a material selected from the group consisting of:
   polyethyleneterepthalate (PET), polyetheretherketone (PEEK), polysulfone, polytetrafluroethylene (PTFE), expanded polytetrafluroethylene (ePTFE), fluorinated ethylene propylene (FEP), polycarbonate urethane, a polyolefin, silicone, and polyurethane.

18. A method for deploying a stent-graft in a distal location in a lumen from a proximal location outside the lumen, the method comprising:
   (a) making an incision in a wall of the lumen;
   (b) introducing a stent-graft into the lumen, the stent-graft comprising: a stent having a wound distal end, a braided midsection, and a proximal end; and a graft having a supported portion lining or covering at least a portion of the stent, and an unsupported portion extending proximally beyond the proximal end of the stent, wherein the unsupported portion has a means for allowing severing of its length within a patient's body and enables an overall length of the stent-graft to be adjusted;
   (c) deploying the stent-graft in the lumen beginning at the distal end of the stent such that an extension of the unsupported portion of the graft extends through the incision in the lumen wall; and (d) severing the lumen and attaching a proximal end of the graft to a distal end of the severed lumen by anastamosis.

19. The method of claim 18, wherein step (d) comprises severing an excess portion of the extension prior to performing the anastamosis.

20. The method of claim 18, wherein step (b) comprises introducing the stent-graft into the lumen using an introducer, optionally over a guidewire, and step (c) comprises removing the introducer and optional guidewire from the lumen after deploying the stent-graft.

21. The method of claim 18, wherein the stent distal end extends distally beyond a distal end of the graft and the method further comprises allowing intraluminal tissue growth on the stent distal end to provide additional anchoring for the stent-graft.

22. The method of claim 18, wherein the lumen comprises an aorta and the method comprises aorto-uni-iliac treatment of an abdominal aortic aneurysm, the method comprising deploying the distal end of the stent distal of the aneurysm and deploying the proximal end of the stent in a first iliac artery in a location distal of the femoral artery in step (c), and the method further comprises the steps of:

(e) deploying an occluder in a second iliac artery to prevent reverse vascular flow into the aneurysm; and (f) providing one or more bypasses to provide vascular flow from the first iliac to the second iliac and to any other lumen occluded by installation of the stent-graft.

23. The method of claim 18 further comprising prior to step (a) deploying a portion of a bifurcated prosthesis in the lumen, the bifurcated prosthesis having a trunk, a first depending section, and a second depending section, wherein deploying the stent-graft comprises sealing off the first depending section from communication of fluid between the trunk and the first depending section and extending the stent-graft through the second depending section.

24. The method of claim 23 comprising deploying the distal end of the stent-graft inside the bifurcated prosthesis.

25. The method of claim 23 comprising deploying the distal end of the stent-graft distally of a distal end of the bifurcated prosthesis.

* * * * *